United States Patent [19]

Namiki et al.

[11] Patent Number: 4,714,758
[45] Date of Patent: Dec. 22, 1987

[54] SURFACTANT COMPOSED OF ACYLATED COLLAGEN OR ACYLATED GELATINE AND A PRODUCTION PROCESS THEREOF

[75] Inventors: Tetsuro Namiki, Ome; Masayasu Furuse, Sagamihara; Yoshimitsu Kuroyanagi, Hachioji; Teruo Miyata, Tokyo, all of Japan

[73] Assignee: Koken Co., Ltd., Tokyo, Japan

[21] Appl. No.: 845,441

[22] Filed: Mar. 28, 1986

[30] Foreign Application Priority Data

Apr. 10, 1985 [JP] Japan ................................ 60-74408

[51] Int. Cl.⁴ .......................... C08H 1/06; C09H 7/00; B01F 17/30
[52] U.S. Cl. .................................... 530/354; 252/356; 435/273; 530/356
[58] Field of Search .......................... 530/354–356; 435/273; 252/356

[56] References Cited

U.S. PATENT DOCUMENTS

| | | | |
|---|---|---|---|
| 2,525,753 | 10/1950 | Yutzy et al. | 530/354 |
| 2,827,419 | 3/1958 | Tourtellotte et al. | 530/354 X |
| 2,956,880 | 10/1960 | Gates, Jr. et al. | 530/354 X |
| 3,108,995 | 10/1963 | Tourtellotte et al. | 530/354 |
| 3,497,358 | 2/1970 | Sieg et al. | 530/354 X |
| 4,140,537 | 2/1979 | Luck et al. | 530/356 X |
| 4,223,984 | 9/1980 | Miyata et al. | 530/356 X |
| 4,234,475 | 11/1980 | Sokol | 530/354 X |
| 4,260,228 | 4/1981 | Miyata | 530/356 X |
| 4,424,208 | 1/1984 | Wallace et al. | 530/356 X |
| 4,557,764 | 12/1985 | Chu | 530/356 X |
| 4,592,864 | 6/1986 | Miyata et al. | 530/356 |

*Primary Examiner*—Howard E. Schain
*Attorney, Agent, or Firm*—Sherman and Shalloway

[57] ABSTRACT

This invention relates to a surfactant composed of acylated collagen or acylated gelatine produced by the acylation of the side chain amino radicals of collagen or gelatine with an aliphatic acid having 2–26 carbon atoms and a dicarboxylic acid having 2–8 carbon atoms and a production process thereof. Since it has less toxicity and irritation against the human body and can dissolve in a neutral solution of pH 6–8 in the form of molecular dispersion, the surfactant is especially suitable for use in the field of cosmetic and foodstuff industries.

11 Claims, No Drawings

SURFACTANT COMPOSED OF ACYLATED COLLAGEN OR ACYLATED GELATINE AND A PRODUCTION PROCESS THEREOF

FIELD OF THE INVENTION

This invention pertains to a surfactant and a production process thereof; more particularly, this invention pertains to a surfactant not only having less toxicity and irritation against the human body but also being suitable for use as an emulsifier or an antiseptic for cosmetics, medicines and foodstuffs with increased water-solubility or hydrophilicity in the neutral condition.

DESCRIPTION OF THE PRIOR ART

Nowadays surfactants are widely used in various industrial fields and their variety is numerous indeed. However, as their use is on the increase, there have appeared problems with effects on the human body and on the environment by virtue of their pollutional effect. Their safety has thus become a very important factor in addition to their effectiveness; especially, in cosmetic and foodstuff industries the safety to the human body is required. Meanwhile, recently, surfactants causing less roughening of hands have been put on the market in the cosmetic field, but in terms of toxicity and irritation to the human body there are very few which are satisfactory. Under the circumstances, the present inventors, for the first time, produced a surfactant composed of acylated collagen or acylated gelatine, produced by acylating collagen, a constituent of living bodies, or gelatine, a heat-denatured product of collagen, with an aliphatic acid. The acylated collagen and the acylated gelatine could be dissolved and molecularly dispersed in an acidic solution near pH 3, but could not dissolve in a neutral solution from pH 6–8. Therefore, they were inconvenient for use in the neutral region neighboring pH 7 where the surfactant is most frequently used for manufacturing cosmetics and foodstuffs. Consequently, the employment of the surfactant had to be limited narrowly.

THE SUMMARY OF THE INVENTION

The inventors have thus made an intensive study to eliminate the drawback and provide a better surfactant so that acylated collagen or acylated gelatine can molecularly dissolve in a neutral solution and finally accomplished the invention. That is, the invention relates to a surfactant composed of acylated collagen or acylated gelatine produced by the acylation of the side chain amino radicals of collagen or gelatine with an aliphatic acid having 2 to 26 carbon atoms and a dicarboxylic acid having 2 to 8 carbon atoms.

DETAILED DESCRIPTION OF THE INVENTION

Referring now to the aliphatic acid used for acylation, for example, acetic acid, propionic acid, lactic acid, n-valeric acid, caproic acid, heptanoic acid, caprylic acid, capric acid, lauric acid, myristic acid, palmitic acid, stearic acid, ricinoleic acid, oleic acid, linoleic acid, 1,2-hydroxystearic acid, arachidinic acid, behenic acid, cerotic acid, etc. can be listed; any of these aliphatic acids are equally usable for this aim. However, propionic acid, heptanoic acid and myristic acid are desirable for the aim in particular. Also, among the dicarboxylic acids used for acylation are aliphatic dicarboxylic acids, such as malonic acid, succinic acid, glutaric acid, maleic acid, 2-methylmaleic acid, 2,3-dimethylmaleic acid, etc. and aromatic dicarboxylic acids like phthalic acid. Any of these dicarboxylic acids are likewise usable for the acylation, but succinic acid is the most desirable of all. (Hereinafter, the acylation by the use of succinic acid is referred to as succinylation.)

Incidentally, the oleophilicity of the surfactant of this invention can be increased by acylating part of the side chain amino radicals of collagen or gelatine with a saturated aliphatic monocarboxylic acid with 2 to 26 carbon atoms; furthermore, the isoelectric point of the surfactant of this invention can be varied widely to about 4.5 so as to solubilize the surfactant even in a neutral region of pH 6–8 by acylating part or the whole of the remaining amino radicals. In this way, an effective surfactant with good solubility, increased hydrophilicity and molecular dispersibility in a neutral solution can be obtained.

The acylation rate of the surfactant can also be varied in a wide range in compliance with the sorts of aliphatic acid and the ratio of an aliphatic acid to a dicarboxylic acid to use. Generally, however, the surfactant becomes more oleophilic as the carbon number of the aliphatic acid and the acylation rate increase. In respect to the dicarboxylic acid, the surfactant becomes more hydrophilic and accordingly easier to dissolve in a neutral solution with pH 6–8 as the acylation rate increase. Usually, however, it is most desirable for the surfactant that the acylation rate by means of the aliphatic acid is about 5–40% and the acylation rate by means of the dicarboxylic acid is about 60–95%.

As stated above, the surfactant of this invention is produced by the partial acylation of the side chain amino radicals of collagen or gelatine with the aliphatic acid or the functional derivative thereof and the subsequent acylation of the same with the dicarboxylic acid or the functional derivative thereof. It is equally produced, however, by the acylation of the same with the aliphatic acid or the functional derivative thereof after the antecedent acylation of the same with the dicarboxylic acid or the functional derivative thereof.

Upon causing the acylation reaction, an anhydride is most convenient for use in both the aliphatic acid and the dicarboxylic acid in terms of the easiness of completing the reaction. In an embodiment of this invention, the pH of collagen or gelatine solution is adjusted to 8–14. Part of $\epsilon$-amino radicals of the collagen or gelatine molecule is acylated by means of the aliphatic acid anhydride with stirring while the temperature is being maintained at 25° C. and below in the case of collagen or at 30°–40° C. in the case of gelatine. Thereafter, part or the whole of the remaining $\epsilon$-amino radicals is acylated by means of the dicarboxylic acid anhydride in the same condition as the above.

This invention will be understood more readily in refference to the following examples; however, these examples are intended to illustrate the invention and are not to be construed to limit the scope of the invention.

EXAMPLE 1

Fifteen grams of atelocollagen (containing about 0.006 mole of $\epsilon$-NH$_2$) is dissolved in 500 ml of water and the pH of the aqueous solution is adjusted to 12 by the use of NaOH. Twenty milliliters of acetone in which 0.002 mole of propionic acid anhydride dissolves is added slowly to the solution and reaction is caused at room temperatures between 20° and 25° C. for 3 hours.

The pH of the solution under reaction was always kept at 3 by adding a 1N NaOH aqueous solution because it tends to lower because of the presence of free propionic acid. As a result of determining the acylation rate according to the TNBS method, it proved to be 20% after the reaction.

After the pH of the partially acylated collagen solution was adjusted to 10, acetone containing 0.024 mole of succinic acid anhydride was added to the solution gradually with stirring and reaction was caused at room temperatures between 20° and 25° C. Since the pH of the solution tended to lower because of the presence of free succinic acid in the course of the reaction, it was maintained at 10 by adding a 1N NaOH aqueous solution.

After the reaction, the pH was adjusted to 4.5 in order to precipitate acylated-succinylated collagen, which was then collected by a centrifuge worked at 5,000 rpm for 30 minutes. The collagen precipitate was rinsed with water 3 times, dehydrated with the same amount of ethanol 3 times and then dried. In this way, a propionic acid-acylated and succinylated collagen was produced. The amino radical modification rate (the total acylation rate) proved to be 98% as a result of the determination according to the TNBS method.

An acid-soluble collagen and a salt-soluble collagen used in place of the aterocollagen showed the same result as the above respectively.

EXAMPLE 2

Fifteen grams of gelatine (containing 0.006 mole of $\epsilon$-$NH_2$) was dissolved in 150 ml of water. After the pH of the solution was adjusted to 12, 20 ml of acetone in which 0.002 mole of heptanoic acid dissolved was added thereto. Acylation was carried out at temperatures between 35° and 40° C. in accordance with the same operational procedure as in Example 1. The acylation rate of the gelatine acylated by the heptanoic acid was 25%. The acylated gelatine was succinylated by succinic acid according to the same operational procedure as in Example 1. In this way, a heptanoic acid-acylated and succinylated gelatine was produced. The succinylation rate was 75%.

EXAMPLE 3

Fifteen grams of atelocollagen (containing about 0.006 mole of $\epsilon$-$NH_2$) was dissolved in 500 ml of water at pH 3. The pH was adjusted to 12 by adding a 1N NaOH aqueous solution. While the atelocollagen aqueous solution was being stirred, a solution prepared by mixing 0.002 mole of myristic acid into 5 ml of tetrahydrofuran and then diluted with 15 ml of acetone was added thereto slowly. In this way, a myristic acid-acylated collagen was obtained similarly as in Example 1. The acylation rate was 15%. The primary product was then succinylated by succinic acid anhydride in the same manner as in Example 1; as a result, a myristic acid-acylated-and-succinylated collagen was produced. The succinylation rate was 83%.

EXAMPLE 4

When mixtures composed of water and olive oil in an arbitrary proportion were emulsified by means of a neutral solution of pH 6.5 containing acylated-succinylated collagen or acylated-succinylated gelatine obtained in Examples 1 to 3, emulsions with good dispersion were obtained respectively.

As stated above, from collagen, a constituent of living bodies, and gelatine, a heat-denatured product of collagen, an effective surfactant with less toxicity and irritation against the human body than conventional surfactants has become available by the acylation with an aliphatic monocarboxylic acid and a dicarboxylic acid. Being soluble in water with pH neighboring the neutral region, the surfactant is easy to put to various uses including cosmetics and foodstuffs. Also, it has an effect especially desirable for manufacturing medicines and cosmetics.

What is claimed is:

1. A surfactant comprising acylated collagen or acylated gelatine produced by acylating part of the side chain amino radicals of collagen or gelatine with an aliphatic monocarboxylic acid or a functional derivative thereof having 2 to 26 carbon atoms followed by subsequently acylating part or the whole of the remaining amino radicals with a dicarboxylic acid or a functional derivative thereof having 2 to 8 carbon atoms.

2. A surfactant according to claim 1 in which said aliphatic monocarboxylic acid is selected from the group consisting of proprionic acid, heptanoic acid and myristic acid.

3. A surfactant according to claim 1, in which said dicarboxylic acid is succinic acid.

4. A process for producing a surfactant composed of acylated collagen or acylated gelatine comprising acylating part of the side chain amino radicals of collagen or gelatine with an aliphatic monocarboxylic acid or a functional derivative thereof having 2 to 26 carbon atoms followed by subsequently acylating part or the whole of the remaining amino radicals with a dicarboxylic acid or a functional derivative thereof having 2 to 8 carbon atoms.

5. The process of claim 4 in which said monocarboxylic acid or functional derivative thereof is monocarboxylic acid anhydride.

6. A surfactant according to claim 1 which is the product of acylation of the side chain amino radicals of collagen.

7. A surfactant according to claim 6 in which said collagen is atelocollagen.

8. The process of claim 4 wherein the degree of acylation by the monocarboxylic acid is 5–40% and the degree of acylation by the dicarboxylic acid is 60–95%.

9. A surfactant according to claim 1 which is acylated 5–40% with a monocarboxylic acid and 60–95% with a dicarboxylic acid.

10. A surfactant comprising acylated collagen or acylated gelatine produced by acylating part of the side chain amino radicals of collagen or gelatine with a dicarboxylic acid or a functional derivative thereof having 2 to 8 carbon atoms followed by subsequently acylating part or the whole of the remaining amino radicals with an aliphatic monocarboxylic acid or a functional derivative thereof having 2 to 26 carbon atoms.

11. A process for producing a surfactant composed of acylated collagen or acylated gelatine comprising acylating part of the side chain amino radicals of collagen or gelatine with a dicarboxylic acid or a functional derivative thereof having 2 to 8 carbon atoms followed by subsequently acylating part or the whole of the remaining amino radicals with an aliphatic monocarboxylic acid or a functional derivative thereof having 2 to 26 carbon atoms.

* * * * *